(12) United States Patent
Lal (10) Patent No.: US 9,629,535 B2
(45) Date of Patent: Apr. 25, 2017

(54) COLONOSCOPE CLOSURE DEVICE

(71) Applicant: Tanmay Lal, Akron, OH (US)

(72) Inventor: Tanmay Lal, Akron, OH (US)

(73) Assignee: UNIVERSITY HOSPITALS OF CLEVELAND, Cleveland, OH (US)

( * ) Notice: Subject to any disclaimer, the term of this patent is extended or adjusted under 35 U.S.C. 154(b) by 0 days.

(21) Appl. No.: 13/938,397

(22) Filed: Jul. 10, 2013

(65) Prior Publication Data

US 2014/0018625 A1    Jan. 16, 2014

Related U.S. Application Data (60) Provisional application No. 61/669,722, filed on Jul. 10, 2012.

(51) Int. Cl.
*A61B 1/00* (2006.01)
*A61B 1/31* (2006.01)
*A61B 1/04* (2006.01)

(52) U.S. Cl.
CPC ............ *A61B 1/31* (2013.01); *A61B 1/00082* (2013.01); *A61B 1/00154* (2013.01)

(58) Field of Classification Search
CPC .......... A61B 1/00082; A61B 17/12136; A61B 2017/3486; A61B 1/31
USPC ................. 600/102, 114, 115, 116, 207, 208
See application file for complete search history.

(56) References Cited

U.S. PATENT DOCUMENTS

| | | | | | |
|---|---|---|---|---|---|
| 2,548,602 | A | * | 4/1951 | Greenburg | ................... 600/207 |
| 3,805,770 | A | * | 4/1974 | Okada | ...................... A61B 1/31 |
| | | | | | 600/114 |
| 3,831,587 | A | * | 8/1974 | Boyd | ............................ 600/207 |
| 4,776,845 | A | * | 10/1988 | Davis | ....................... A61B 1/31 |
| | | | | | 600/114 |
| 5,795,289 | A | * | 8/1998 | Wyttenbach | .................. 600/207 |
| 5,941,815 | A | * | 8/1999 | Chang | ........................... 600/114 |
| 6,142,931 | A | * | 11/2000 | Kaji | ............................... 600/114 |
| 6,358,266 | B1 | * | 3/2002 | Bonutti | ......................... 606/190 |
| 2006/0271095 | A1 | * | 11/2006 | Rauker | ..................... A61B 1/31 |
| | | | | | 606/197 |
| 2007/0213661 | A1 | * | 9/2007 | Gobel | ......................... 604/96.01 |
| 2008/0091146 | A1 | * | 4/2008 | Solovay et al. | ............. 604/174 |
| 2010/0249524 | A1 | | 9/2010 | Ransden et al. | |
| 2012/0157784 | A1 | * | 6/2012 | Kleyman et al. | ............. 600/208 |

FOREIGN PATENT DOCUMENTS

WO    WO 2008/115505    9/2008

* cited by examiner

*Primary Examiner* — Timothy J Neal
(74) *Attorney, Agent, or Firm* — Richard M. Klein; Fay Sharpe LLP (57) ABSTRACT

The present application is directed to a colonoscope closure device. The colonoscope closure device includes an inner tubular member that defines an entry way sized to accommodate a colonoscope, an intermediate tubular member surrounding the inner tubular member, and an expandable sealing member at least partially surrounding the intermediate tubular member. The colonoscope closure device serves to prevent the escape of air during a colonoscopy procedure.

12 Claims, 8 Drawing Sheets

COLONOSCOPE CLOSURE DEVICE

CROSS-REFERENCE TO RELATED APPLICATIONS

This application claims priority to U.S. Provisional Patent Application Ser. No. 61/669,722, filed on Jul. 10, 2012. The entirety of that application is hereby fully incorporated by reference.

FIELD OF INVENTION

The present disclosure relates generally to accessories for use in colonoscopy procedures and, more particularly, to a colonoscope closure device to prevent the escape of air and to assist advancement of a colonoscope during examination of a patient.

BACKGROUND

A colonoscopy is a procedure for inspecting the inside of a patient's colon using a long flexible tube that is commonly referred to as a colonoscope. A colonoscopy can detect inflamed tissue, ulcers, and abnormal growths. The procedure is used to look for early signs of colorectal cancer and can help doctors diagnose unexplained changes in bowel habits, abdominal pain, bleeding from the anus, and weight loss.

A colonoscopy is useful in locating and removing polyps, diagnosing cancers, finding causes of intestinal bleeding and following patients with previous polyps or cancers. Polyps are small growths inside the large intestine. They usually are benign, but occasionally may have a focus of cancer in the tip. Often, these can be removed at the time of the colonoscopy.

A colonoscopy allows the examiner to view the inside of the colon and to find disease processes which often do not show on x-ray examinations, or which cannot be diagnosed with certainty by such an examination. It constitutes a major diagnostic and therapeutic advance for diseases of the large intestine. The ability to remove polyps with this instrument means that the patient can avoid a major operation.

SUMMARY OF INVENTION

The present invention is directed to a colonoscope closure device configured to prevent or minimize the escape of air during a colonoscopy procedure. The colonoscope closure device includes an expandable sealing member that can be inflated and deflated.

One aspect of the disclosed technology relates to a colonoscope closure device that includes an inner tubular member that defines an entry way sized to accommodate a colonoscope; an intermediate tubular member coupled to and substantially surrounding the inner tubular member; and an expandable sealing member coupled to and at least partially surrounding the intermediate tubular member, wherein the expandable sealing member is configured to have an inflated condition and a deflated condition.

According to one feature, the inner tubular member is made of a flexible material.

According to one feature, the inner tubular member is made of a polymer gel.

According to one feature, the intermediate tubular member is rigid.

According to one feature, the expandable sealing member has a length approximately equal to a length of the inner tubular member and a length of the intermediate tubular member.

According to one feature, the expandable sealing member has a length that is shorter than a length of the inner tubular member and a length of the intermediate tubular member.

According to one feature, the expandable sealing member is approximately round in cross section.

According to one feature, the expandable sealing member is approximately oval in cross section.

According to one feature, the inner tubular member and the intermediate tubular member each have a length of about 4.0 inches to about 5.0 inches and a diameter of about 1.5 inches to about 2.0 inches.

According to one feature, the expandable sealing member has a length of about 1.0 inches.

According to one feature, the expandable sealing member has a deflated diameter of about 1.0 inches to about 1.5 inches and an inflated diameter of about 1.0 inches to about 2.0 inches.

According to one feature, the expandable sealing member is configured to accept about 10 mL to about 50 mL of fluid.

According to one feature, the expandable sealing member is configured to accept about 10 mL to about 50 mL of air.

According to one feature, the colonoscope closure device has a substantially uniform diameter when deflated.

According to one feature, the colonoscope closure device has a distal end and a proximal end, and wherein the proximal end has a larger diameter than the distal end when deflated.

According to one feature, the expandable sealing member is a balloon member configured to expand upon the introduction of fluid.

According to one feature, the balloon member defines a generally toroidal shape.

According to one feature, the colonoscope closure device includes an inflation device in fluid communication with the expandable sealing member.

According to one feature, the inflation device is an air pump.

According to one feature, the inflation device comprises a manual pump.

According to one feature, the manual pump includes a release valve.

Another aspect of the disclosed technology relates to a method of performing a colonoscopy on a subject. The method includes inserting a colonoscope through a colonoscope closure device. The colonoscope closure device includes an inner tubular member that defines an entry way sized to accommodate a colonoscope; an intermediate tubular member coupled to and substantially surrounding the inner tubular member; and an expandable sealing member coupled to and at least partially surrounding the intermediate tubular member, wherein the expandable sealing member is configured to have an inflated condition and a deflated condition. The method further includes inserting the colonoscope closure device and the colonoscope into the subject's anal canal; and inflating the colonoscope closure device.

According to one feature, inflating includes inflating the expandable sealing member.

According to one feature, inflating includes directing air into the expandable sealing member.

According to one feature, inflating includes directing air into the expandable sealing member using a manual inflation device.

According to one feature, the manual inflation device is a hand pump.

According to one feature, the method includes advancing the colonoscope through the colonoscope closure device into the subject anal canal.

According to one feature, inserting includes lubricating the colonoscope prior to insertion through the colonoscope closure device.

According to one feature, the inner tubular member is made of a flexible material.

According to one feature, the inner tubular member is made of a polymer gel.

According to one feature, the intermediate tubular member is rigid.

According to one feature, the expandable sealing member has a length approximately equal to a length of the inner tubular member and a length of the intermediate tubular member.

According to one feature, the expandable sealing member has a length that is shorter than a length of the inner tubular member and a length of the intermediate tubular member.

According to one feature, the expandable sealing member is approximately round in cross section.

According to one feature, the expandable sealing member is approximately oval in cross section.

According to one feature, the inner tubular member and the intermediate tubular member each have a length of about 4.0 inches to about 5.0 inches and a diameter of about 1.5 inches to about 2.0 inches.

According to one feature, the expandable sealing member has a length of about 1.0 inches.

According to one feature, the expandable sealing member has a deflated diameter of about 1.0 inches to about 1.5 inches and an inflated diameter of about 1.0 inches to about 2.0 inches.

According to one feature, the expandable sealing member is configured to accept about 10 mL to about 50 mL of fluid.

According to one feature, the expandable sealing member is configured to accept about 10 mL to about 50 mL of air.

Another aspect of the disclosed technology relates to a colonoscope closure device that includes an expandable sealing member that defines an entry way sized to accommodate a colonoscope, wherein the expandable sealing member is configured to have an inflated condition and a deflated condition.

According to one feature, the expandable sealing member has an external dimension sized for insertion into an opening of a patient's anal canal.

According to one feature, the colonoscope closure device includes a distal end configured for insertion into the opening of the patient's anal canal and a proximal end being configured to expand to substantially block a release of air injected into a patient's colon.

According to one feature, the colonoscope closure device has a length of about 4.0 inches to about 5.0 inches and a diameter of about 1.5 inches to about 2.0 inches.

According to one feature, the expandable sealing member has a length of about 1.0 inches.

According to one feature, the expandable sealing member has a deflated diameter of about 1.0 inches to about 1.5 inches and an inflated diameter of about 1.0 inches to about 2.0 inches.

According to one feature, the expandable sealing member is configured to accept about 10 mL to about 50 mL of fluid.

According to one feature, the expandable sealing member is configured to accept about 10 mL to about 50 mL of air.

According to one feature, the colonoscope closure device has a substantially uniform diameter when deflated.

According to one feature, the colonoscope closure device has a distal end and a proximal end, and wherein the proximal end has a larger diameter than the distal end when deflated.

According to one feature, the colonoscope closure device includes an inflation device in fluid communication with the expandable sealing member.

According to one feature, the inflation device is an air pump.

According to one feature, the inflation device comprises a manual pump.

According to one feature, the manual pump includes a release valve.

These and further features of the present invention will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the spirit and terms of the claims appended thereto.

Features that are described and/or illustrated with respect to one embodiment may be used in the same way or in a similar way in one or more other embodiments and/or in combination with or instead of the features of the other embodiments.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Likewise, elements and features depicted in one drawing may be combined with elements and features depicted in additional drawings. Moreover, in the drawings, like reference numerals designate corresponding parts throughout the several views.

DETAILED DESCRIPTION

To illustrate aspects of the disclosed technology in a clear and concise manner, the drawings may not necessarily be to scale and certain features may be shown in somewhat schematic form.

During a colonoscopy procedure, air can be injected into the patient to expand the colon so that adequate visualization is possible, as well as to assist advancement of the colonoscope through the patient's colon. In some cases, especially those in which the patient is under anesthesia, the external and/or internal sphincter does not contract. This condition allows air to escape, causing decreased visualization and inability to advance the colonoscope.

The present disclosure recognizes shortcomings with conventional colonoscopy procedures and provides a colonoscope closure device that will aid in preventing the escape of air during a colonoscopy procedure. As is discussed more fully below, the colonoscope closure device includes an expandable sealing member configured to have an inflated condition and a deflated condition to prevent or minimize the escape of air introduced into a patient's colon during a colonoscopy procedure.

Aspects of the disclosed technology will be described in connection with a colonoscopy procedure in which a colonoscope is introduced into a patient's rectal cavity for examination of the patient's colon.

Referring now to FIGS. 1-12, a colonoscope closure device 10 is provided. In accordance with one exemplary embodiment, the colonoscope closure device includes an inner tubular member 12 that defines an entry way sized to accommodate a colonoscope. For example, the inner tubular member can define an entry way that is approximately round with a diameter of about one-half (½) inches to about 1.0 inches and a length of about two inches to about five inches. The inner tubular member can have a thickness of about one-sixteenth (1/16) inches to about one-eighth (⅛) inches. It will be appreciated that other exemplary dimensions may be employed without departing from the scope of the present invention. In accordance with one embodiment, the inner tubular member is made of a suitable flexible or pliable material, such as suitable polymer gel material. Exemplary suitable materials include medical-grade plastics and polymers.

In the illustrated exemplary embodiment, the inner tubular member is coupled to and at least partially surrounded by an intermediate tubular member 14. The intermediate tubular member 14 is coupled to the inner tubular member 12, for example, by a suitable adhesive or by chemical bonding. In accordance with one embodiment, the intermediate tubular member 14 can have a length approximately equal to the length of the inner tubular member 12. Alternatively, the intermediate tubular member 14 can have a length that is shorter than or longer than the length of the inner tubular member 12.

The intermediate tubular member 14 can be made of a suitable rigid plastic or other suitable rigid or substantially rigid material. Exemplary suitable materials include medical grade plastics and polymers. In accordance with one exemplary embodiment, the intermediate tubular member has a diameter of about one-half (½) inches to about 2.0 inches and a thickness of about one-sixteenth (1/16) inches to about one-eighth (⅛) inches.

The intermediate tubular member 14 is coupled to and at least partially surrounded by an expandable sealing member 16. The expandable sealing member 16 is coupled to the intermediate tubular member 14, for example, by a suitable adhesive or by chemical bonding. The expandable sealing member 16 is configured to be selectively inflated and deflated, providing a seal to prevent or minimize the escape of air injected into the patient's colon during the colonoscopy procedure. In accordance with one exemplary embodiment, the expandable sealing member 16 can have a length approximately equal to the length of the inner tubular member 12 and/or the intermediate tubular member 14. Alternatively, the expandable sealing member 16 can have a length that is shorter than the length of the inner tubular member 12 and/or the intermediate tubular member 14.

It will be appreciated that the expandable sealing member 16 can take on a variety of geometries. For example, the expandable sealing member may be approximately round in cross section. Alternatively, the expandable sealing member may be approximately oval in cross section. In accordance with one exemplary embodiment, the inner tubular member 12 and the intermediate tubular member 14 can each have a length of about 4.0 inches to about 5.0 inches and a diameter of about 0.5 inches to about 2.0 inches. In this embodiment, the expandable sealing member may have a length approximately equal to the length of the inner tubular member and/or the intermediate tubular member. Alternatively, the expandable sealing member can have a length of about 1.0 inches.

In accordance with one embodiment, the expandable sealing member can have a deflated diameter of about 1.0 inches to about 2.0 inches and an inflated diameter of about 1.0 inches to about 2.0 inches. In one embodiment, the expandable sealing member is configured to have a substantially uniform diameter when deflated. Alternatively, where the expandable sealing member has a distal end and proximal end, the proximal end can have a larger diameter than the distal end when deflated. The expandable sealing member can be configured to accept an amount of fluid (e.g., air) sufficient to provide a seal when the colonoscope closure device is positioned in the opening of the patient's anal canal. For example, the expandable sealing member can be configured to accept about 10 milliliters to about 50 milliliters of fluid, for example, about 10 milliliters to about 50 milliliters of air.

Figures 1, 2:
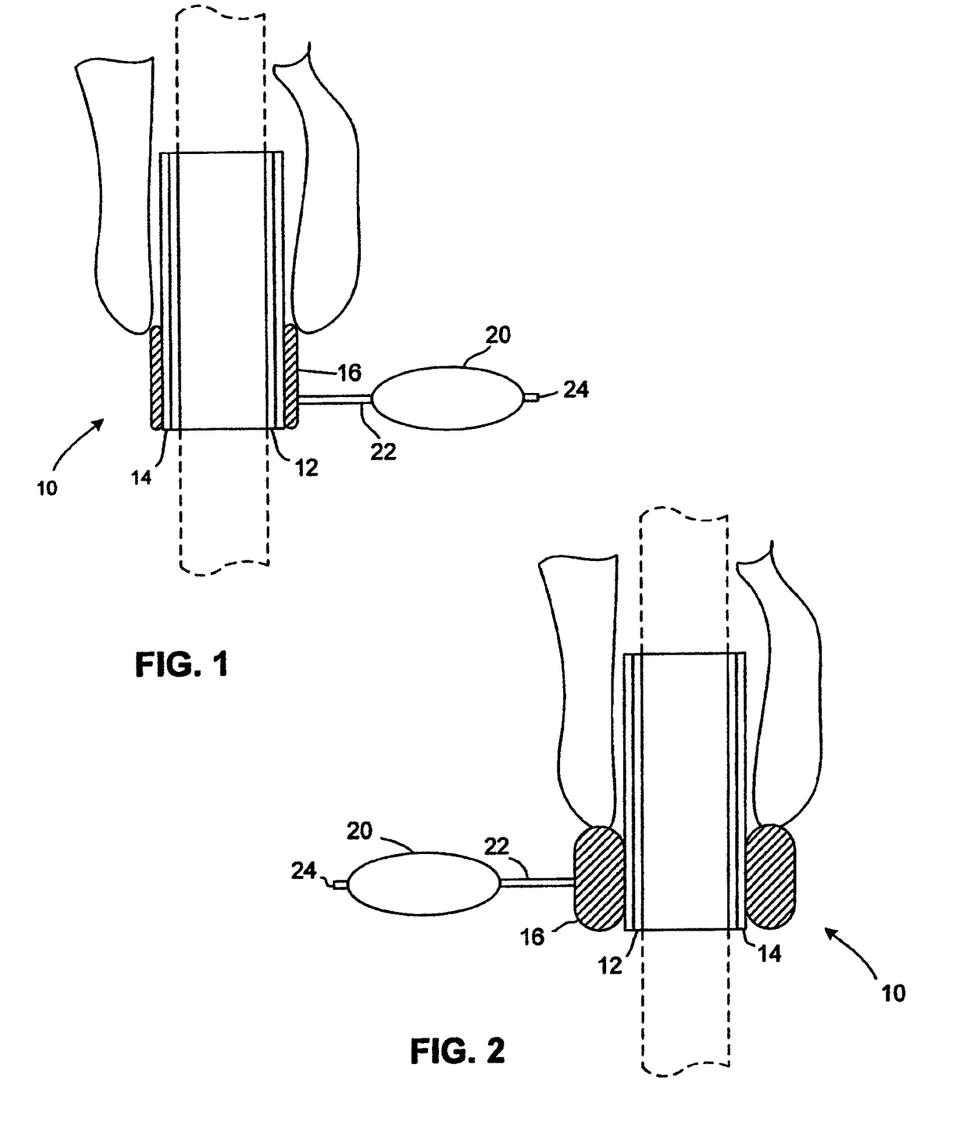
FIG. 1 is a cross-sectional view of a colonoscope closure device in a deflated condition in accordance with one aspect of the disclosed technology.
FIG. 2 is a cross-sectional view of a colonoscope closure device in an inflated condition in accordance with one aspect of the disclosed technology.
Figure 3:
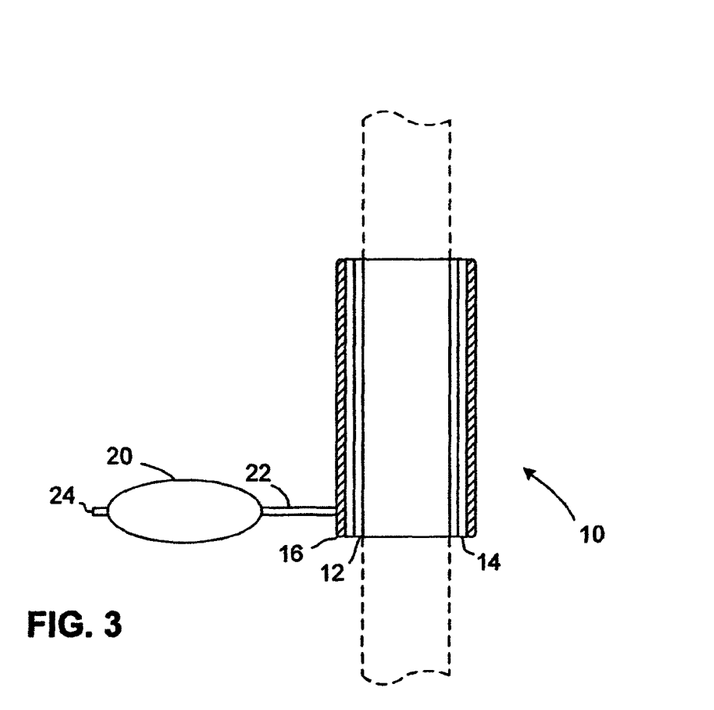
FIG. 3 is a cross-sectional view of a colonoscope closure device in a deflated condition in accordance with one aspect of the disclosed technology.
Figure 4:
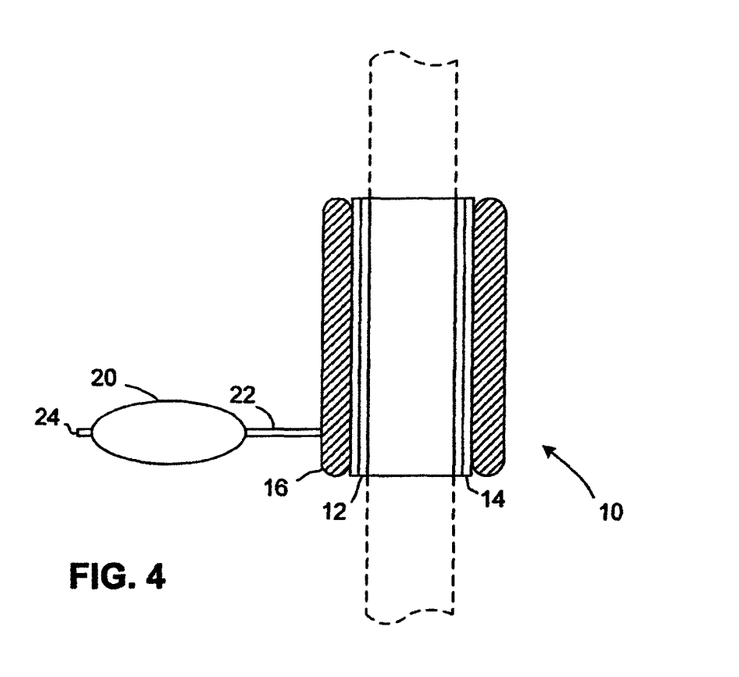
FIG. 4 is a cross-sectional view of a colonoscope closure device in an inflated condition in accordance with one aspect of the disclosed technology.
Figure 5:
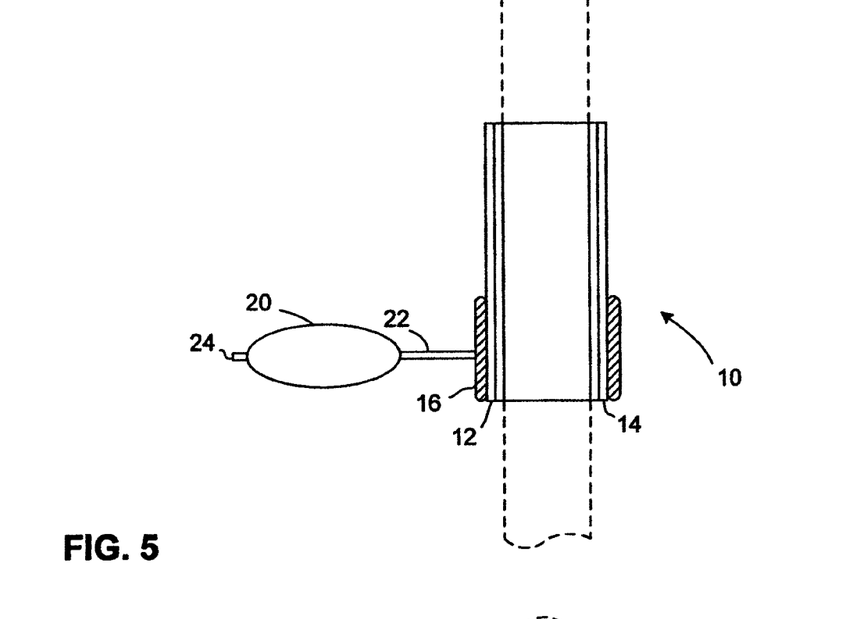
FIG. 5 is a cross-sectional view of a colonoscope closure device in a deflated condition in accordance with one aspect of the disclosed technology.
Figure 6:
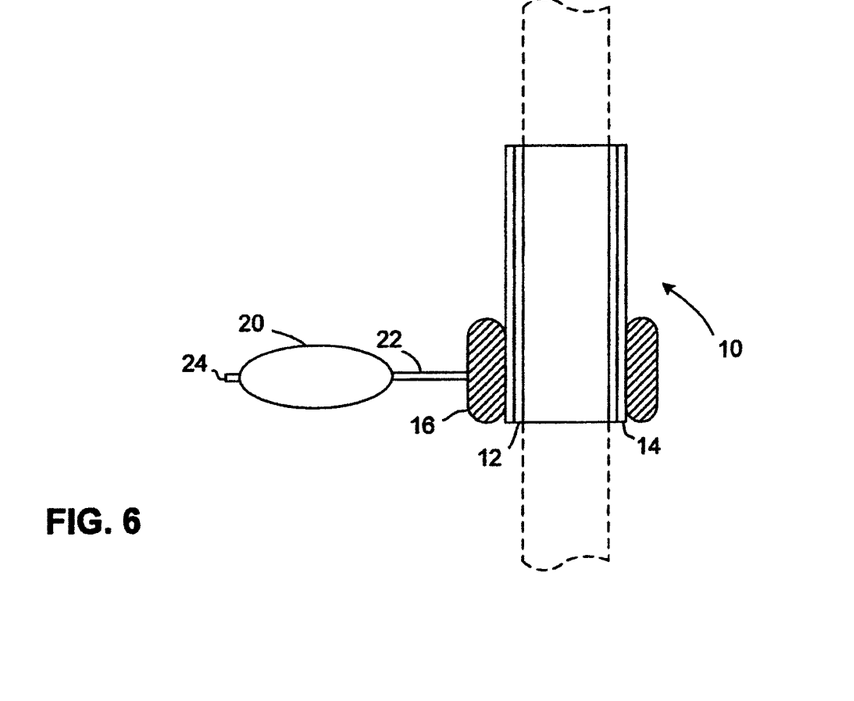
FIG. 6 is a cross-sectional view of a colonoscope closure device in an inflated condition in accordance with one aspect of the disclosed technology.
Figure 7:
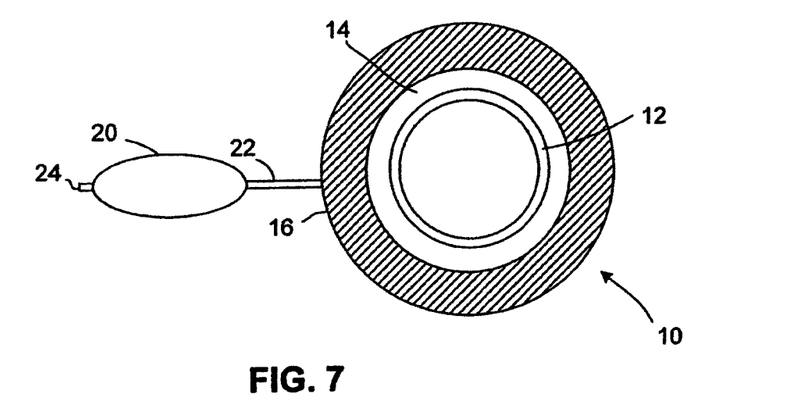
FIG. 7 is an end view of a colonoscope closure device in a deflated condition in accordance with one aspect of the disclosed technology.
Figure 8:
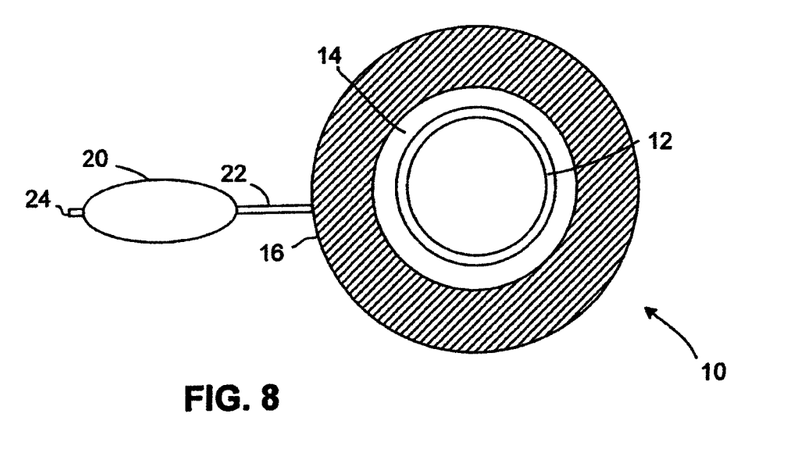
FIG. 8 is an end view of a colonoscope closure device in an inflated condition in accordance with one aspect of the disclosed technology.
Figure 9:
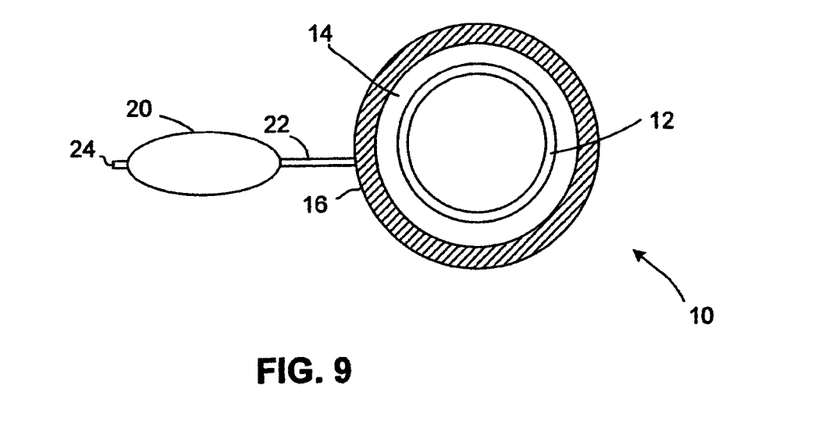
FIG. 9 is an end view of a colonoscope closure device in a deflated condition in accordance with one aspect of the disclosed technology.
Figure 10:
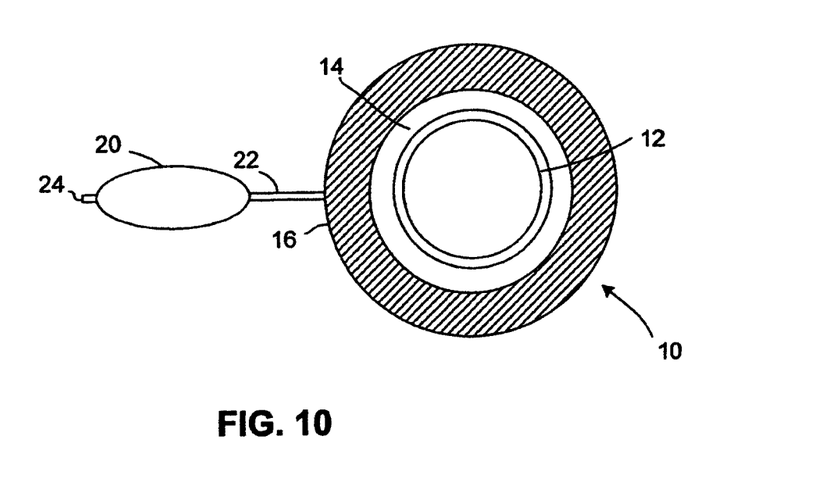
FIG. 10 is an end view of a colonoscope closure device in an inflated condition in accordance with one aspect of the disclosed technology.
Figure 11:
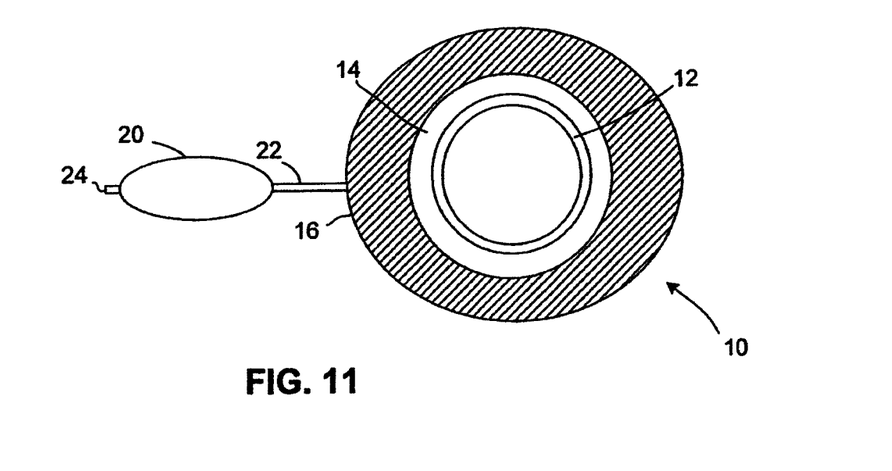
FIG. 11 is an end view of a colonoscope closure device in a deflated condition in accordance with one aspect of the disclosed technology.
Figure 12:
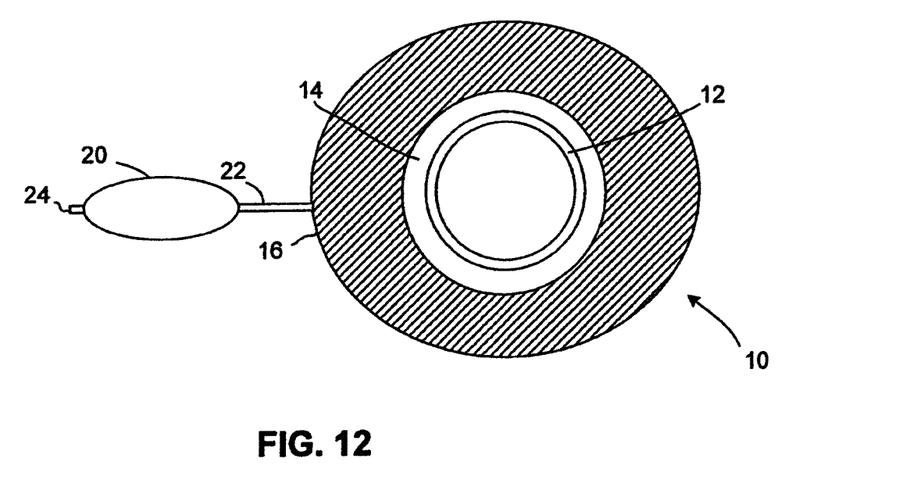
FIG. 12 is an end view of a colonoscope closure device in an inflated condition in accordance with one aspect of the disclosed technology.

As shown in FIG. 4, the colonoscope closure device includes an inflation device 20 in fluid communication with the expandable sealing member 16, for example, by a suitable connector 22 such as a tube or the like. In accordance with one embodiment, the inflation device 20 is an air pump, for example, a manual pump that may be operated by the user of the colonoscope closure device. The manual pump can include a release valve 24 for deflating the expandable sealing member once the expandable sealing member has been inflated.

Figure 13:
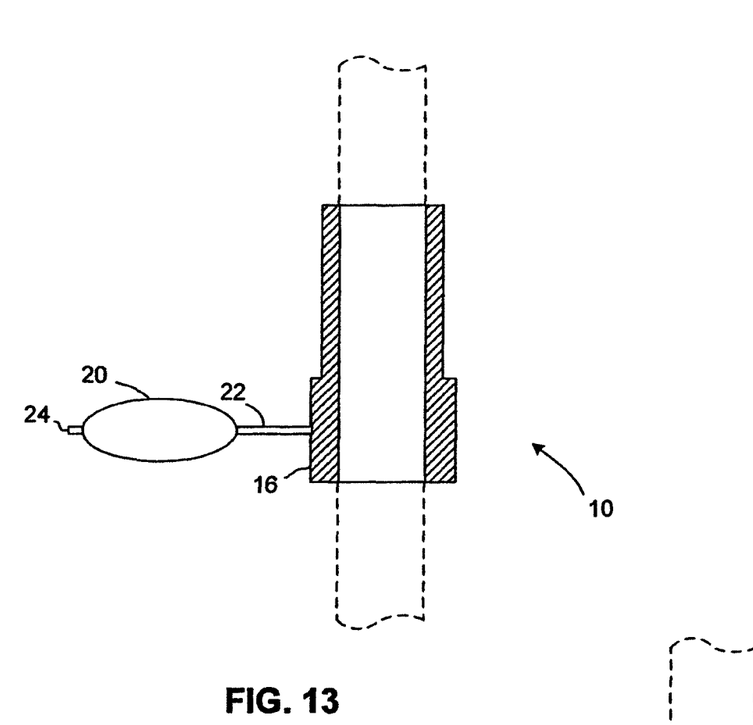
FIG. 13 is a cross-sectional view of a colonoscope closure device in a deflated condition in accordance with one aspect of the disclosed technology.
Figure 14:
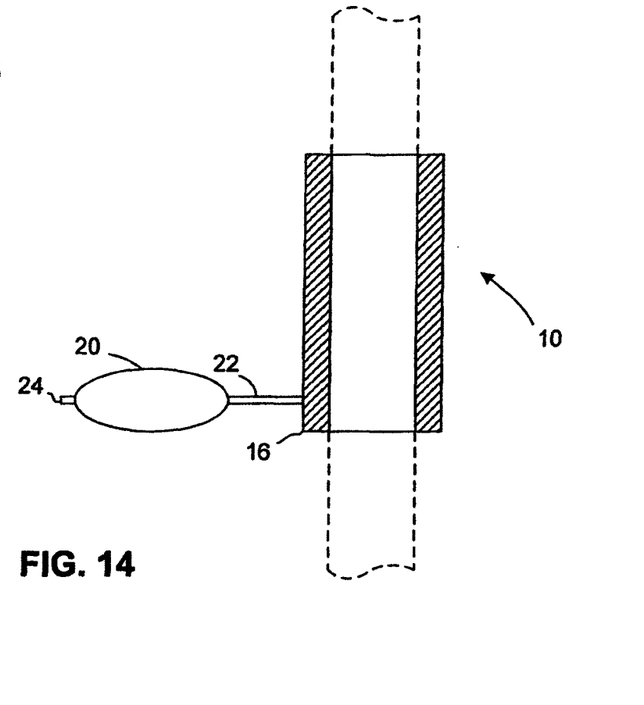
FIG. 14 is a cross-sectional view of a colonoscope closure device in an inflated condition in accordance with one aspect of the disclosed technology.

In accordance with another embodiment, the colonoscope closure device 10 can be configured as a single piece of plastic or other polymer that can be selectively inflated and deflated to prevent or otherwise minimize the escape of air injected into the patient's colon during the colonoscopy procedure. For example, as shown in FIG. 13 and FIG. 14, the colonoscope closure device can include an expandable sealing member 16 that defines an entry way sized to accommodate a colonoscope where the expandable sealing member is configured to have an inflated condition and a deflated condition. For example, FIG. 13 shows an exemplary embodiment in which the colonoscope closure device is formed as a single inflatable layer having a variable diameter or cross section when in a deflated state, while FIG. 14 shows an embodiment in which the colonoscope closure device has a substantially uniform diameter or cross section when in a deflated state. In this embodiment, the expandable sealing member alone serves as the colonoscope closure device without making use of other layers or structures (e.g., without making use of an inner tubular member and/or an intermediate tubular member). Persons of ordinary skill in the art will appreciate that other geometries of the colonoscope closure device and expandable sealing member may be employed without departing from the scope of the present invention.

Figure 15:
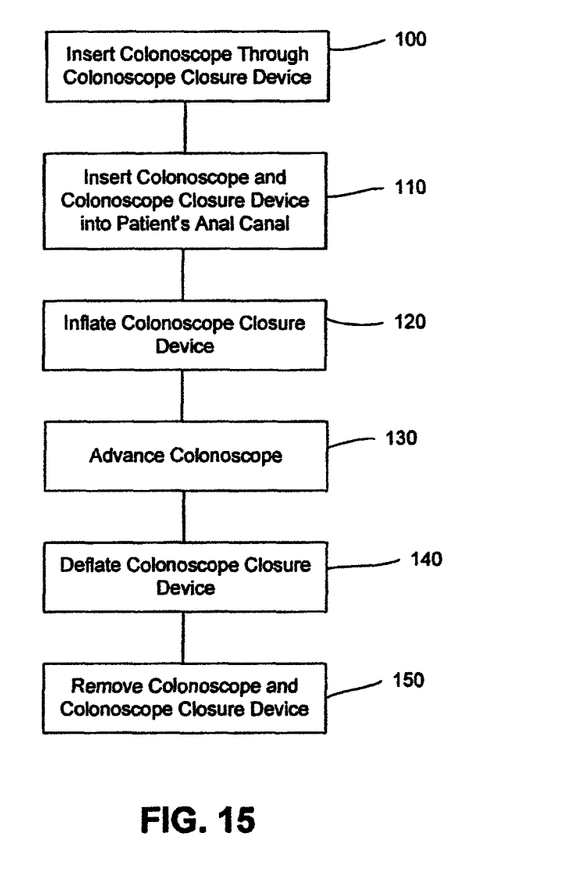
FIG. 15 is a flow chart illustrating a colonoscopy method in accordance with one aspect of the disclosed technology.

The above-described embodiments of a colonoscope closure device can be used in a colonoscopy procedure. In accordance with one embodiment, the method of performing a colonoscopy on a subject includes inserting a colonoscope closure device (step 100). It will be appreciated that the colonoscope closure device may take on any of the configurations described above. For example, the colonoscope closure device can include an inner tubular member that defines an entry way sized to accommodate a colonoscope, an intermediate tubular member coupled to and substantially surrounding the inner tubular member, and an expandable sealing member coupled to and at least partially surrounding the intermediate tubular member, wherein the expandable sealing member is configured to have an inflated condition and a deflated condition.

The colonoscope and/or the inner tubular member may be provided with a suitable lubricant to aid sliding movement of the colonoscope through the inner tubular member of the colonoscope closure device. Once the colonoscope has been inserted through the colonoscope closure device, the colonoscope closure device and the colonoscope are inserted into the patient's anal canal (step 110). After insertion of the colonoscope and the colonoscope closure device into the patient's anal canal, the colonoscope closure device can be inflated (step 120) using any suitable inflation means, such as those described above. At step 130, the colonoscope can be advanced into and through the patient's colon along with optionally injecting air into the patient's colon. Once the inspection of the patient's colon is complete, the colonoscope closure device can be deflated (step 140), for example, by using a release valve on the manual inflation pump. The colonoscope and colonoscope closure device can then be removed (step 150) from the patient's anal canal, thereby concluding the procedure.

As is discussed above, the provision of a colonoscope closure device having an expandable sealing member improves colonoscopy procedures by preventing or minimizing the escape of air injected into a patient's colon during the procedure, thereby increasing visualization within the colon and advancement of the colonoscope during the procedure.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:
1. A colonoscope closure device consisting of:
an inner tubular member that defines an entry way sized to accommodate a colonoscope and that is made of a flexible or pliable material;
an intermediate tubular member coupled to the inner tubular member and having a length approximately equal to a length of the inner tubular member, the intermediate tubular member substantially surrounding the entire length of the inner tubular member, the intermediate tubular member being made of a substantially rigid material; and
an expandable sealing member coupled to and at least partially surrounding the intermediate tubular member, wherein the expandable sealing member is configured to have an inflated condition and a deflated condition, and wherein the expandable sealing member has a length shorter than the length of the inner tubular member and the length of the intermediate tubular member; and
an inflation device in fluid communication with the expandable sealing member;
wherein the colonoscope closure device has a distal end configured for insertion into an opening of a patient's anal canal and a proximal end being configured to expand to substantially block a release of air injected into a patient's colon; and
wherein the expandable sealing member is located at a terminal edge of the proximal end of the colonoscope closure device.
2. The colonoscope closure device of claim 1, wherein the expandable sealing member is approximately round or approximately oval in cross section.

3. The colonoscope closure device of claim 1, wherein the length of the inner tubular member and the intermediate tubular member are each about 4.0 inches to about 5.0 inches and the inner tubular member and the intermediate tubular member each have a diameter of about 1.5 inches to about 2.0 inches.

4. The colonoscope closure device of claim 1, wherein the expandable sealing member has a deflated diameter of about 1.0 inches to about 2.0 inches and an inflated diameter of about 1.0 inches to about 2.0 inches.

5. The colonoscope closure device of claim 1, wherein the expandable sealing member is configured to accept about 10 mL to about 50 mL of a fluid or air.

6. The colonoscope closure device of claim 1, wherein the colonoscope closure device has a substantially uniform diameter when deflated.

7. The colonoscope closure device of claim 1, wherein the proximal end has a larger diameter than the distal end when deflated.

8. The colonoscope closure device of claim 1, wherein the expandable sealing member is a balloon member configured to expand upon the introduction of fluid.

9. The colonoscope closure device of claim 1, wherein the flexible or pliable material of the inner tubular member is a polymer gel.

10. A method of performing a colonoscopy on a subject, the method comprising:
    inserting a colonoscope through a colonoscope closure device, the colonoscope closure device consisting of:
        an inner tubular member that defines an entry way sized to accommodate a colonoscope and that is made of a flexible or pliable material;
        an intermediate tubular member coupled to the inner tubular member and having a length approximately equal to a length of the inner tubular member, the intermediate tubular member substantially surrounding the entire length of the inner tubular member, the intermediate tubular member being made of a substantially rigid material; and
        an expandable sealing member coupled to and at least partially surrounding the intermediate tubular member, wherein the expandable sealing member is configured to have an inflated condition and a deflated condition, and wherein the expandable sealing member has a length that is shorter than a length of the inner tubular member and a length of the intermediate tubular member; and
        an inflation device in fluid communication with the expandable sealing member;
        wherein the colonoscope closure device has a distal end configured for insertion into an opening of a patient's anal canal and a proximal end being configured to expand to substantially block a release of air injected into a patient's colon; and
        wherein the expandable sealing member is located at a terminal edge of the proximal end of the colonoscope closure device;
    inserting the colonoscope closure device and the colonoscope into the subject's anal canal; and
    inflating the colonoscope closure device using the inflation device.

11. The method of claim 10, wherein inflating includes inflating the expandable sealing member.

12. The method of claim 10, further comprising advancing the colonoscope through the colonoscope closure device into the subject's anal canal.

* * * * *